US006787672B2

(12) United States Patent
Potter et al.

(10) Patent No.: US 6,787,672 B2
(45) Date of Patent: Sep. 7, 2004

(54) SUBSTITUTED CHALCONES AS THERAPEUTIC COMPOUNDS

(75) Inventors: Gerard Andrew Potter, Leicestershire (GB); Paul Crispin Butler, Leicestershire (GB); Elugba Wanogho, Leicestershire (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 10/239,757

(22) PCT Filed: Mar. 26, 2001

(86) PCT No.: PCT/GB01/01341
§ 371 (c)(1),
(2), (4) Date: Sep. 6, 2002

(87) PCT Pub. No.: WO01/72680
PCT Pub. Date: Oct. 4, 2001

(65) Prior Publication Data
US 2003/0100538 A1 May 29, 2003

(30) Foreign Application Priority Data
Mar. 27, 2000 (GB) .............................................. 0007401

(51) Int. Cl.[7] ........................ C07C 49/115; A61K 31/12
(52) U.S. Cl. ...................... 568/327; 568/331; 568/334; 568/337; 514/681; 514/685; 514/688
(58) Field of Search ................................. 568/327, 331, 568/334, 337, 14, 17, 24, 25; 514/109, 111, 125, 681, 685, 688

(56) References Cited

U.S. PATENT DOCUMENTS

| 4,279,930 A | 7/1981 | Hall et al. |
| 5,430,062 A | 7/1995 | Cushman et al. |
| 5,691,373 A | 11/1997 | Berryman et al. |
| 6,214,886 B1 | 4/2001 | Potter et al. |

FOREIGN PATENT DOCUMENTS

| GB | 2198945 A | 6/1988 |
| JP | 61-076433 A | 4/1986 |
| JP | 02-142717 | 5/1990 |
| JP | 05-246932 | 9/1993 |
| JP | 08-188546 A | 7/1996 |
| WO | WO 95/05376 | 2/1995 |
| WO | WO 97/12246 | 4/1997 |
| WO | WO 99/00114 | 1/1999 |
| WO | WO 99/40056 | 8/1999 |
| WO | 01/46110 | 6/2001 |

OTHER PUBLICATIONS

Barrie, S.E., et al., 1989, "Inhibition of 17–hydroxylase/C17–C20 Lyase by Bifluranol and Its Analogues," *J. Steroid Biochem.*, vol. 33, No. 6, pp. 1191–1195.

Carmichael, J., 1987, "Evaluation of a Tetrazolium–based Semiautomated Colorimetric Assay: Assessment of Chemosensitivity Testing," *Cancer Research*, vol. 47, p. 936–942.

Ducki, S., et al., 1998, "Potent Antimitotic and Cell growth Inhibitory Properties of Substituted Chalcones," *BioMed. Chem. Lett.*, vol. 8, pp. 1051–1056.

Mosmann, T., 1983, "Rapid Colorimetric Assay for Cellular Growth and Survival: Application to Proliferation and Cytotoxicity Assays," *Journal of Immunological Methods*, vol. 65, pp. 55–63.

Murray, G.I., et al., 1997, "Tumour–specific Expression of Cytochrome P450 CYP1B1," *Cancer Research*, vol. 57, pp. 3026–3031.

Pettit, G.R., et al., 1995, "Antineoplastic agents 322. Synthesis of Combretastatin A–4 Prodrugs," *Anticancer Drug Design*, vol. 10, pp. 299–309.

Spink, D.C., et al., 1994, "The Effects of 2,3,7,8–Tetrachlorodibenzo–p–dioxin on Estrogen Metabolism in MCF–7 Breast Cancer Cells: Evidence for Induction of a Novel 17β–Estradiol 4–hydroxylase," *J. Steroid Biochem. Mol. Biol.*, vol. 51, No. 5/6, pp. 251–258.

Sutter, T.R., et al, 1994, "Complete cDNA sequence of a human dioxin–inducible mRNA identifies a new gene subfamily of cytochrome P450 that maps onto chromosome 2," *J. Biol. Chem.*, vol. 269, No. 18, pp. 13092–13099.

Yamashita, D.S., et al, 1994, "Design, Synthesis and Evaluation of Dual Domain FKBP Ligands," *Bioorg. Med. Chem. Lett.*, vol. 4, No. 2, pp. 325–328.

Iwata et al., 1999, "Antitumorigenic Activities of Chalcones. I. Inhibitory Effects of Chalcone Derivatives on 32Pi–Incorporation into Phospholipids of HeLa Cells Promoted by 12–O–Tetradecanoyl–phorbol 13–Acetate (TPA)," *Biol. Pharm. Bull.*, Japan, vol. 18, No. 12, pp. 1710–1713.

Shibata, 1994, "Anti–Tumorigenic Chalcones," *Stem Cells*, vol. 12, pp. 44–52.

(List continued on next page.)

*Primary Examiner*—Johann Richter
*Assistant Examiner*—Sikarl A. Witherspoon
(74) *Attorney, Agent, or Firm*—Nixon & Vanderhye P.C.

(57) ABSTRACT

This invention pertains to substituted chalcones, specifically substituted 1-(4-methoxyphenyl)-3-(3,5-dimethoxyphenyl) prop-1-en-3-ones, which have therapeutic application, for example, as potent antiproliferative agents and antiinflammatory agents, and which have the formula (I) wherein: X is —H, —OH, —OC(=O)R$_3$, —OS(=O)$_2$OH, or —OP(=O)(OH)$_2$; Y is —H or a C$_{1-4}$alkyl group; Z is —H or —OCH$_3$; R$_1$ is —H, a C$_{1-4}$alkyl group, or C$_{1-4}$fluoroalkyl group; R$_2$ is —H, a C$_{1-4}$alkyl group, or C$_{1-4}$fluoroalkyl group; and, R$_3$ is —H, a C$_{1-6}$alkyl group, a C$_{3-20}$ heterocyclyl group, or a C$_{5-20}$aryl group; and pharmaceutically acceptable salts, esters, and protected forms thereof. The present invention also pertains to pharmaceutical compositions comprising such compounds, and the use of such compounds and compositions, both in vitro and in vivo, for both diagnosis and treatment of, for example, proliferative conditions, such as cancer, and inflammatory conditions.

89 Claims, 1 Drawing Sheet

OTHER PUBLICATIONS

Sogawa et al., 1993, "3,4–Dihydroxychalcones as Potent 5–Lipoxygenase and Cyclooxygenase Inhibitors," J. Med. Chem., vol. 36, No. 24, pp. 3904–3909.

De Wet et al., 2001, "Sequence Requirements of the ATP–Binding Site within the C–Terminal Nucleotide–Binding Domain of Mouse P–Glycoprotein: Structure–Activity Relationships for Flavenoid Binding," Biochemistry, vol. 40, pp. 10382–10391.

Hsieh et al., 2000, "Synthesis and Anti–Inflammatory Effect of Chalcones," J. Pharm. Pharmacol., vol. 52, pp. 163–171.

Tanaka et al., 2001, "Influence of Natural and Synthetic Compounds on Cell Surface Expression of Cell Adhesion Molecules, ICAM–1 and VCAM–1," Planta. Med., vol. 67, pp. 108–113.

Parmar et al., 1997, "Anti–Invasive Activity of Alkaloids and Polyphenolics in Vitro," Bioorg. & Med. Chem., vol. 5, No. 8, pp. 1609–1619.

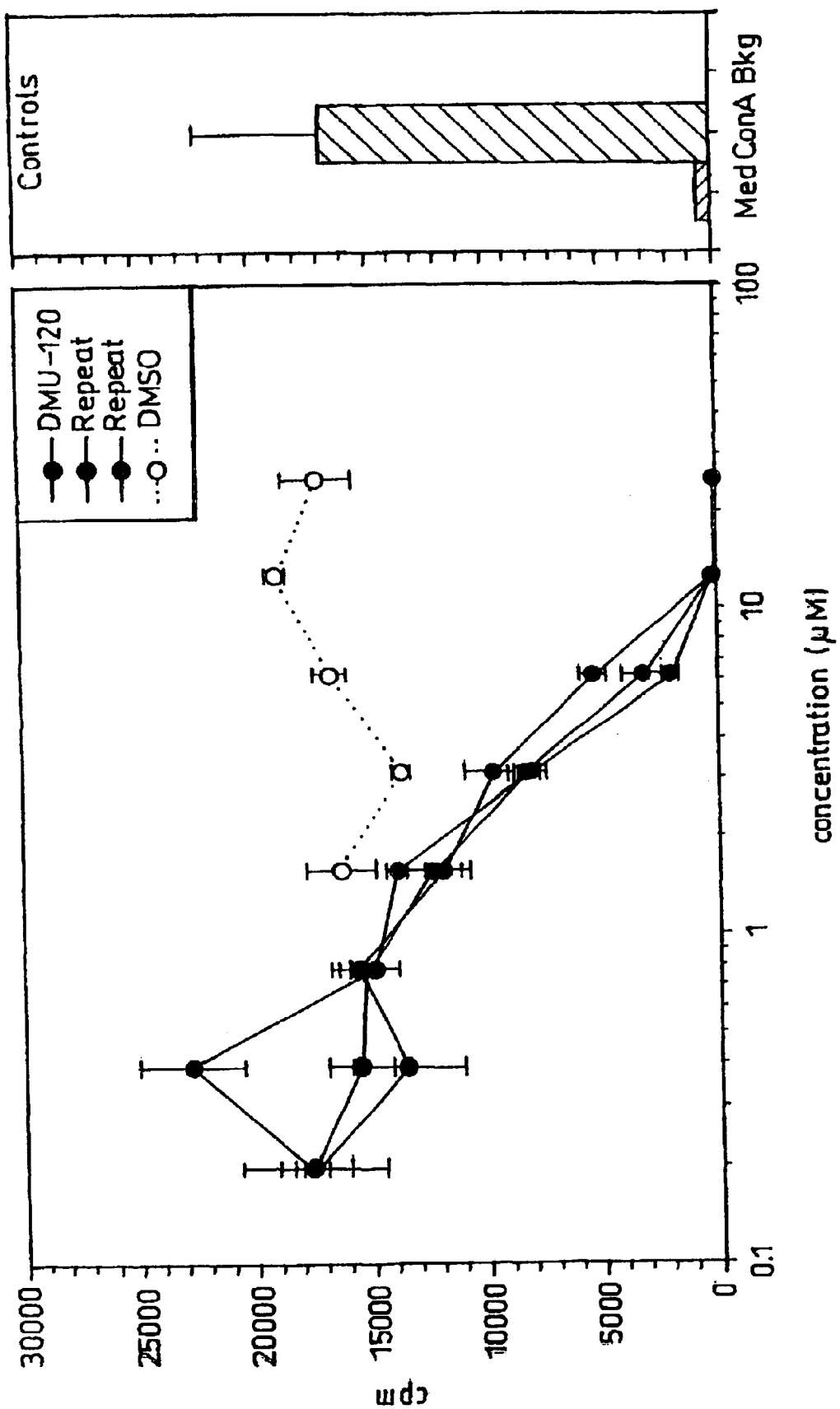

SUBSTITUTED CHALCONES AS THERAPEUTIC COMPOUNDS

This application is the U.S. national phase of international application PCT/GB01/01341 filed 26 Mar. 2001, which designated the U.S.

RELATED APPLICATION

This application claims priority to United Kingdom (GB) Patent Application No. 0007401.3, filed Mar. 27, 2000, which is incorporated herein by reference in its entirety.

TECHNICAL FIELD

This invention pertains to substituted chalcones, specifically substituted 1-(4-methoxyphenyl)-3-(3,5-dimethoxyphenyl)prop-1-en-3-ones, which have therapeutic application, for example, as potent antiproliferative agents and antiinflammatory agents. The present invention also pertains to pharmaceutical compositions comprising such compounds, and the use of such compounds and compositions, both in vitro and in vivo, for both diagnosis and treatment of, for example, proliferative conditions, such as cancer, and inflammatory conditions.

BACKGROUND

Chalcone, also known as chalkone, benzylideneacetophenone, benzalacetophenone, and phenyl styryl ketone, is 1,3-diphenyl-2-propen-1-one, and has the following structure:

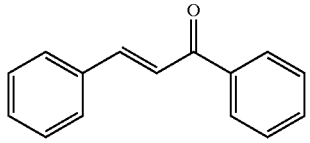

A number of substituted chalcones have been prepared, with one or more substituents on the styryl phenyl group (left), the acyl phenyl group (right), and/or the double bond carbon atoms.

A number of substituted chalcones having a 3,4,5-trimethoxyphenyl group (as the acyl phenyl group) have been reported to have excellent antitumour activity (Hiromitsu, 1996; Ducki et al., 1998; Akihiko, 1986). These compounds have the following general formula:

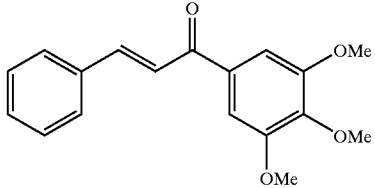

Surprisingly and unexpectedly, it has now been found that substituted chalcones having a 3,5-dimethoxyphenyl group (as the acyl phenyl group) have highly potent anticancer activity and/or antiinflammatory activity.

One such compound, shown below (Chemical Abstracts Registry Number 169803-62-7), has been reported (Berryman et al., 1995, 1997), but only as an intermediate used in the preparation of 5H-furan-2-one compounds, which are reported to have use as endothelin antagonists. Specifically, the compound shown below was prepared from 3,5-dimethoxyacetophenone and 4-methoxybenzaldehyde (Example 122, page 146, in Berryman et al., 1995), subsequently derivatised (Examples 123 and 124, pages 147 and 148), and then used as a reagent to prepare a number of 5H-furan-2-one compounds (Examples 125–135, pages 148–158).

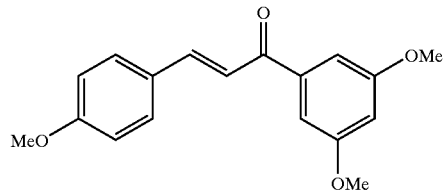

SUMMARY OF THE INVENTION

One aspect of the present invention pertains to compounds of the formula:

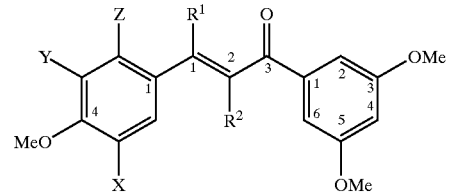

wherein:

X is —H, —OH, —OC(=O)$R^3$, —OS(=O)$_2$OH, or —OP(=O)(OH)$_2$;

Y is —H or a $C_{1-4}$alkyl group;

Z is —H or —OCH$_3$;

$R^1$ is —H, a $C_{1-4}$alkyl group, or $C_{1-4}$fluoroalkyl group;

$R^2$ is —H, a $C_{1-4}$alkyl group, or $C_{1-4}$fluoroalkyl group; and, $R^3$ is —H, a $C_{1-6}$alkyl group, a $C_{3-20}$heterocyclyl group, or a $C_{5-20}$aryl group;

and pharmaceutically acceptable salts, esters, and protected forms thereof; with the proviso that X, Y, Z, $R^1$, and $R^2$ are not all —H.

In one preferred embodiment, X is —H.
In one preferred embodiment, X is —OH, —OC(=O)$R^3$, —OS(=O)$_2$OH, or —OP(=O)(OH)$_2$.
In one preferred embodiment, X is —OH.
In one preferred embodiment, Y is —H. —CH$_3$ or —CH$_2$CH$_3$.
In one preferred embodiment, Y is —H.
In one preferred embodiment, Y is —CH$_3$ or —CH$_2$CH$_3$.
In one preferred embodiment, Z is —H.
In one preferred embodiment, Z is —OCH$_3$.
In one preferred embodiment, $R^1$ and $R^2$ are independently —H, —CH$_3$, —CH$_2$CH$_3$, —CF$_3$, —CH$_2$CF$_3$, or —CF$_2$CF$_3$.
In one preferred embodiment, both $R^1$ and $R^2$ are —H.
In one preferred embodiment, $R^3$ is —CH$_3$. —CH$_2$CH$_3$, —C(CH$_3$)$_3$, or -Ph.

Another aspect of the present invention pertains to a composition comprising a compound as described herein (without the proviso) and a pharmaceutically acceptable carrier.

Another aspect of the present invention pertains to a method of treating a proliferative condition in a patient comprising administering to said patient a therapeutically-effective amount of a compound as described herein (without the proviso). In one preferred embodiment, the proliferative condition is cancer.

Another aspect of the present invention pertains to a compound as described herein (without the proviso), for use in a method of treatment of the human or animal body.

Another aspect of the present invention pertains to use of a compound as described herein (without the proviso) for the manufacture of a medicament for use in the treatment of a proliferative condition. In one preferred embodiment, the proliferative condition is cancer.

Another aspect of the present invention pertains to a method of prophylactically treating a proliferative condition in a patient comprising administering to said patient a therapeutically-effective amount of a compound as described herein (without the proviso). In one preferred embodiment, the proliferative condition is cancer.

Another aspect of the present invention pertains to the use of a compound as described herein (without the proviso) for the manufacture of a medicament for use in the prophylactic treatment of a proliferative condition. In one preferred embodiment, the proliferative condition is cancer.

Another aspect of the present invention pertains to a method of treating a inflammatory condition in a patient comprising administering to said patient a therapeutically-effective amount of a compound as described herein (without the proviso). In one preferred embodiment, the inflammatory condition is rheumatoid arthritis, rheumatic fever, osteoarthritis, inflammatory bowel disease, psoriasis, or bronchial asthma.

Another aspect of the present invention pertains to the use of a compound as described herein (without the proviso) for the manufacture of medicament for use in the treatment of an inflammatory condition. In one preferred embodiment, the inflammatory condition is rheumatoid arthritis, rheumatic fever, osteoarthritis, inflammatory bowel disease, psoriasis, or bronchial asthma.

Another aspect of the present invention pertains to a compound as described herein (without the proviso), wherein X is —H, for use in a method of diagnosis of the human or animal body. In one preferred embodiment, the diagnosis is for the presence of tumour cells expressing the CYP1B1 enzyme.

Another aspect of the present invention pertains to the use of a compound as described herein (without the proviso), wherein X is —H, for the presence of tumour cells expressing the CYP1B1 enzyme.

Another aspect of the present invention pertains to a method of diagnosis of a patient for the presence of tumour cells expressing the CYP1B1 enzyme, comprising:

(a) administering to the patient a compound as described herein (without the proviso), wherein X is —H;

(b) determining the amount of the corresponding hydroxylated metabolite, wherein X is —OH, which is subsequently produced; and, (c) correlating the amount with the presence or absence of the tumour cells in the patient.

As will be appreciated by one of skill in the art, features and preferred embodiments of one aspect of the invention will also pertain to other aspects of the invention.

BRIEF DESCRIPTION OF THE DRAWINGS

FIG. 1 is a graph of counts per minute (cpm) versus concentration of Compound II (DMU-120) for the splenocyte anti-proliferation assay described in Example 10.

DETAILED DESCRIPTION OF THE INVENTION

Compounds

One aspect of the present invention pertains to compounds of the following formula:

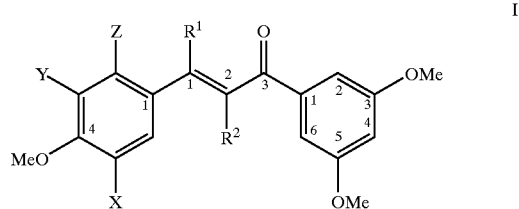

wherein:

X is —H, —OH, —OC(=O)$R^3$, —OS(=O)$_2$OH, or —OP(=O)(OH)$_2$;

Y is —H or a $C_{1-4}$alkyl group;

Z is —H or —OCH$_3$;

$R^1$ is —H, a $C_{1-4}$alkyl group, or $C_{1-4}$fluoroalkyl group;

$R^2$ is —H, a $C_{1-4}$alkyl group, or $C_{1-4}$fluoroalkyl group; and, $R^3$ is —H, a $C_{1-6}$alkyl group, a $C_{3-20}$heterocyclyl group, or a $C_{5-20}$aryl group;

and pharmaceutically acceptable salts, esters, and protected forms thereof.

Insofar as the present invention pertains to compounds, per se, these compounds are as defined herein, with the proviso that X, Y, Z, $R^1$, and $R^2$ are not all —H. However, this proviso does not apply to the present invention in its other aspects, for example, as it pertains to pharmaceutical compositions comprising the compounds, methods of treatment employing the compounds, the compounds for medical use, use of the compounds in the preparation of medicaments, and the like.

Note that the compounds of the present invention are all of the "E" (entgegen) or "trans" form, that is, the (optionally substituted) 4-methoxy-phenyl group (styryl phenyl group) and the 3,5-dimethoxybenzoyl group (acyl phenyl group) are positioned "trans" with respect to one another on the carbon-carbon double bond of the prop-1-ene backbone.

The term "$C_{1-4}$alkyl," as used herein, pertains to monovalent aliphatic saturated alkyl groups having from 1 to 4 carbon atoms. The term "aliphatic," as used herein, pertains to groups which are linear or branched, but not cyclic. Examples of saturated linear $C_{1-4}$alkyl groups include methyl, ethyl, n-propyl, and n-butyl. Examples of saturated branched $C_{1-4}$alkyl groups include iso-propyl, iso-butyl, sec-butyl, tert-butyl. In one preferred embodiment, the $C_{1-4}$alkyl group is methyl or ethyl.

The term "$C_{1-4}$fluoroalkyl group," as used herein, pertains to a $C_{1-4}$alkyl group in which at least one hydrogen atom has been replaced with a fluorine atom. Every hydrogen atom may be replaced with a fluorine atom, in which case the group may conveniently be referred to as a "$C_{1-4}$perfluoroalkyl group." Examples of $C_{1-4}$fluoroalkyl groups include, but are not limited to, —CF$_3$, —CHF$_2$, —CH$_2$F, —CH$_2$CH$_2$F, —CH$_2$CHF$_2$, —CH$_2$CF$_3$, —CF$_2$CF$_3$, and —C(CF$_3$)$_3$. In one preferred embodiment, the $C_{1-4}$fluoroalkyl group is —CF$_3$, —CH$_2$CF$_3$, or —CF$_2$CF$_3$.

The term "$C_{1-6}$alkyl," as used herein, pertains to monovalent alkyl groups having from 1 to 6 carbon atoms, which may be aliphatic or alicyclic, or a combination thereof. The term "aliphatic," as used herein, pertains to groups which are linear or branched, but not cyclic. The term "alicyclic," as used herein, pertains to groups which have one ring, or two or more rings (e.g., spiro, fused, bridged), but which are not aromatic.

Examples of saturated linear $C_{1-6}$alkyl groups include, but are not limited to, methyl, ethyl, n-propyl, n-butyl, and n-pentyl (amyl).

Examples of saturated branched $C_{1-6}$alkyl groups include, but are not limited to, iso-propyl, iso-butyl, sec-butyl, tert-butyl, and neo-pentyl.

Examples of saturated alicylic (carbocyclic) $C_{1-6}$alkyl groups (also referred to as "$C_{3-6}$cycloalkyl" groups) include, but are not limited to, cyclopropyl, cyclobutyl, cyclopentyl, and cyclohexyl, as well as groups which comprise such groups, including, but not limited to, cyclopropylmethyl and cyclohexylmethyl.

The term "$C_{3-20}$heterocyclyl," as used herein, pertains to a monovalent moiety obtained by removing a hydrogen atom from a ring atom of an alicyclic (i.e., non-aromatic cyclic) compound, said compound having one ring, or two or more rings (e.g., spiro, fused, bridged), having from 3 to 20 ring atoms, of which from 1 to 10 are ring heteroatoms, including, but not limited to, nitrogen, oxygen, and sulfur. Preferably, each ring has from 3 to 7 ring atoms, of which from 1 to 4 are ring heteroatoms. "$C_{3-20}$" denotes ring atoms, whether carbon atoms or heteroatoms.

Examples of $C_{3-20}$heterocyclyl groups having one nitrogen ring atom include, but are not limited to, those derived from pyrrolidine, pyrroline, pyrrolinine, piperidine, dihydropyridine, and tetrahydropyridine.

Examples of $C_{3-20}$heterocyclyl groups having one oxygen ring atom include, but are not limited to, those derived from oxolane (tetrahydrofuran), oxole (dihydrofuran), oxane (tetrahydropyran), dihydropyran, and pyran.

Examples of $C_{3-20}$heterocyclyl groups having one sulfur ring atom include, but are not limited to, those derived from thiolane and tetrahydrothiopyran.

Examples of $C_{3-20}$heterocyclyl groups having two nitrogen ring atoms include, but are not limited to, those derived from imidazolidine, imidazoline, and piperazine.

Examples of $C_{3-20}$heterocyclyl groups having one nitrogen ring atom and one oxygen ring atom include, but are not limited to, those derived from tetrahydrooxazole, dihydrooxazole, tetrahydroisoxazole, dihydroiosoxazole, morpholine, tetrahydrooxazine, and dihydrooxazine.

Examples of $C_{3-20}$heterocyclyl groups having one oxygen ring atom and one sulfur ring atom include, but are not limited to, oxathiolane and oxathiane.

The term "$C_{5-20}$aryl," as used herein, pertains to a monovalent moiety obtained by removing a hydrogen atom from a ring atom of an aromatic compound, said compound having one ring, or two or more fused rings, and having from 5 to 20 ring atoms. The ring atoms may be all carbon atoms, as in "carboaryl groups," or may include one or more heteroatoms (including but not limited to oxygen, nitrogen, and sulfur, as in "heteroaryl groups." In the latter case, the group may conveniently be referred to as a "$C_{5-20}$heteroaryl" group, wherein "$C_{5-20}$" denotes ring atoms, whether carbon atoms or heteratoms. Preferably, each ring has from 3 to 7 ring atoms, of which from 0 to 4 are ring heteroatoms.

Examples of $C_{5-20}$aryl groups which do not have heteroatoms (i.e., carboaryl groups) include, but are not limited to, phenyl and naphthyl.

Examples of $C_{5-20}$heteroaryl groups include, but are not limited to, pyrrolyl, imidazolyl, pyrazolyl, triazolyl, pyridyl, pyrazinyl, pyrimidinyl, pyridazinyl, triazinyl, furanyl, thienyl, thiazolyl, isothiazolyl, pyranyl, pyronyl, benzopyronyl, oxazolyl, isoxazolyl, oxadiazolyl, oxatriazolyl, oxathiazolyl, and oxathiazinyl.

The above $C_{1-6}$alkyl, $C_{3-20}$heterocyclyl, and $C_{5-20}$aryl groups may themselves optionally be substituted with one or more substituents. Examples of such substituents include, but are not limited to, $C_{1-6}$alkyl, $C_{3-20}$heterocyclyl, and $C_{5-20}$aryl groups as well as halo, hydroxy, and carboxylic acid groups.

For example, the term "$C_{1-6}$alkyl-$C_{5-20}$aryl," as used herein, describes certain $C_{5-20}$aryl groups which have been substituted with a $C_{1-6}$alkyl group. Examples of such groups include, but are not limited to, tolyl, xylyl, mesityl, and cumenyl.

For example, the term "$C_{5-20}$aryl-$C_{1-6}$alkyl," as used herein, describers certain $C_{1-6}$alkyl groups which have been substituted with a $C_{5-20}$aryl group. Examples of such groups include, but are not limited to, benzyl, tolylmethyl, and phenylethyl.

In one preferred embodiment, X is —H, and Y, Z, $R^1$, and $R^2$ are as defined above. Such compounds may conveniently be referred to herein as "non-hydroxylated compounds."

In one preferred embodiment, X is —OH, —OC(=O)$R^3$, —OS(=O)$_2$OH, or —OP(=O)(OH)$_2$, and Y, Z, $R^1$, $R^2$, and $R^3$ are as defined above.

In one preferred embodiment, X is —OH, and Y, Z, $R^1$, $R^2$, and $R^3$ are as defined above. Such compounds may conveniently be referred to herein as "hydroxylated compounds."

In one preferred embodiment, X is —OC(=O)$R^3$, —OS(=O)$_2$OH, or —OP(=O)(OH)$_2$, and Y, Z, $R^1$, $R^2$, and $R^3$ are as defined above. Such compounds may conveniently be referred to herein as "esterified compounds."

In one preferred embodiment, Y is —H, —CH$_3$, or —CH$_2$CH$_3$, and X and Z are as defined above. In one preferred embodiment, Y is —H, and X and Z are as defined above.

In one preferred embodiment, Z is —H, and X and Y are as defined above.

In one preferred embodiment, $R^1$ and $R^2$ are independently —H, —CH$_3$, —CH$_2$CH$_3$, —CF$_3$, —CH$_2$CF$_3$, or —CF$_2$CF$_3$.

In one preferred embodiment, $R^1$ and $R^2$ are independently —H, —CH$_3$, or —CH$_2$CH$_3$.

In one preferred embodiment, $R^1$ and $R^2$ are independently —H, —CF$_3$, —CH$_2$CF$_3$, or —CF$_2$CF$_3$.

In one preferred embodiment, both $R^1$ and $R^2$ are —H.

In one preferred embodiment, only one of $R^1$ and $R^2$ is —H.

In one preferred embodiment, neither of $R^1$ and $R^2$ is —H.

In one preferred embodiment, one of $R^1$ and $R^2$ is —H, and the other is —CH$_3$, —CH$_2$CH$_3$, —CF$_3$, —CH$_2$CF$_3$, or —CF$_2$CF$_3$.

In one preferred embodiment, $R^3$ is —CH$_3$ (so that —C(=O)$R^3$ is —C(=O)CH$_3$, acetyl); —CH$_2$CH$_3$ (so that —C(=O)$R^3$ is —C(=O)CH$_2$CH$_3$, propionyl); —C(CH$_3$)$_3$ (so that —C(=O)$R^3$ is —C(=O)C(CH$_3$)$_3$, pivaloyl); or -Ph (so that —C(=O)$R^3$ is —C(=O)Ph, benzoyl).

In one preferred embodiment:
X is —H, —OH, —OC(=O)$R^3$, —OS(=O)$_2$OH, or —OP(=O)(OH)$_2$;
Y is —H, —CH$_3$ or —CH$_2$CH$_3$;
Z is —H or —OCH$_3$;
$R^1$ is —H, —CH$_3$, —CH$_2$CH$_3$, —CF$_3$, —CH$_2$CF$_3$, or —CF$_2$CF$_3$;
$R^2$ is —H, —CH$_3$, —CH$_2$CH$_3$, —CF$_3$, —CH$_2$CF$_3$, or —CF$_2$CF$_3$; and,
$R^3$ is —H, —CH$_3$, —CH$_2$CH$_3$, —C(CH$_3$)$_3$, or -Ph In one embodiment, the compound has the following structure, and is referred to herein as Compound II (also referred to as DMU-120, (E)-1-(4-methoxyphenyl)-3-(3,5-dimethoxyphenyl) prop-1-en-3-one):

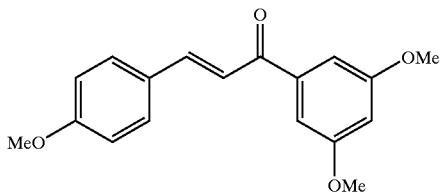

II

In one embodiment, the compound has the following structure, and is referred to herein as Compound III (also referred to as DMU-153, (E)-1-(3-hydroxy-4-methoxyphenyl)-3-(3,5-dimethoxyphenyl)prop-1-en-3-one):

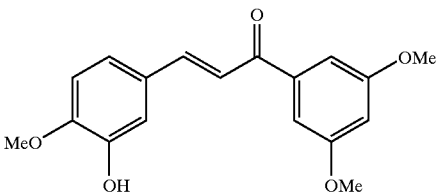

III

In one embodiment, the compound has the following structure, and is referred to herein as Compound IV (also referred to as DMU-162, (E)-1-(2,4-dimethoxyphenyl)-3-(3,5-dimethoxyphenyl)prop-1-en-3-one):

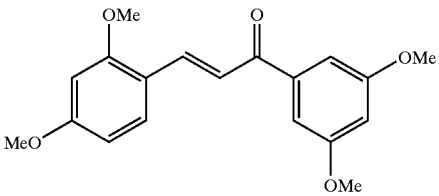

IV

In one embodiment, the compound has the following structure, and is referred to herein as Compound V (also referred to as DMU-436, (E)-2-(4-methoxyphenyl)-4-(3,5-dimethoxyphenyl)but-2-en-4-one):

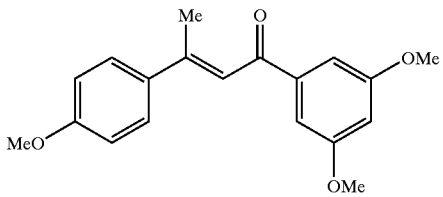

V

In one embodiment, the compound has the following structure, and is referred to herein as Compound VI (also referred to as DMU-428, (E)-1-(4-methoxyphenyl)-2-methyl-3-(3,5-dimethoxyphenyl)prop-1-en-3-one):

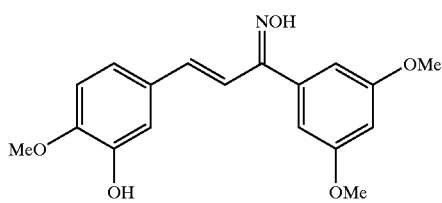

VI

In one embodiment, the compound has the following structure, and is referred to herein as Compound VII (also referred to as DMU-153, (E)-1-(3—Hydroxy-4-methoxyphenyl)-3-(3,5-dimethoxyphenyl)prop-1-en-3-one oxime), wherein the ketone group is protected in the form of a Schiff base:

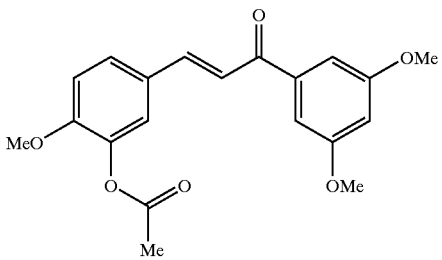

VII

In one embodiment, the compound has the following structure, and is referred to herein as Compound VIII (also referred to as DMU-170, (E)-1-(3-acetoxy-4-methoxyphenyl)-3-(3,5-dimethoxyphenyl)prop-1-en-3-one):

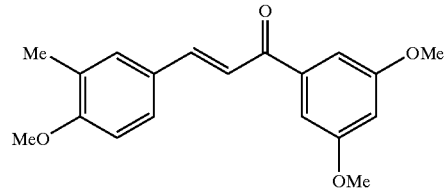

VIII

In one embodiment, the compound has the following structure ((E)-1-(3-methyl-4-methoxyphenyl)-3-(3,5-dimethoxyphenyl)prop-1-en-3-one):

IX

In one embodiment, the compound has the following structure ((E)-1-(3-hydroxy-4-methoxy-5-methylphenyl)-3-(3,5-dimethoxyphenyl)prop-1-en-3-one):

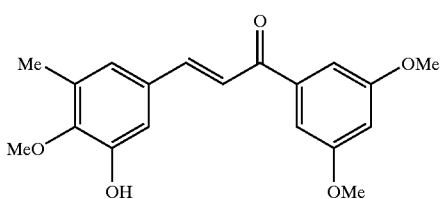

In one embodiment, the compound has the following structure ((E)-1-(2,4-dimethoxy-5-hydroxy-phenyl)-3-(3,5-dimethoxyphenyl)prop-1-en-3-one):

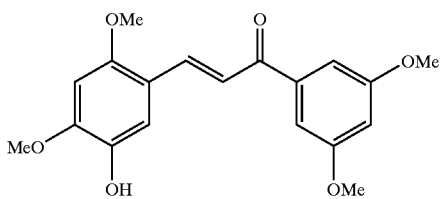

In one embodiment, the compound has the following structure ((E)-1-(2,4-dimethoxy-3-methyl-phenyl)-3-(3,5-dimethoxyphenyl)prop-1-en-3-one):

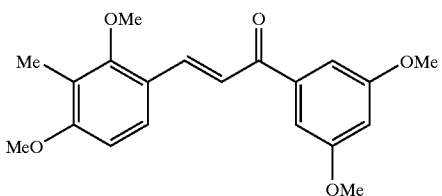

In one embodiment, the compound has the following structure ((E)-1-(2,4-dimethoxy-3-methyl-4-hydroxy-phenyl)-3-(3,5-dimethoxyphenyl)prop-1-en-3-one):

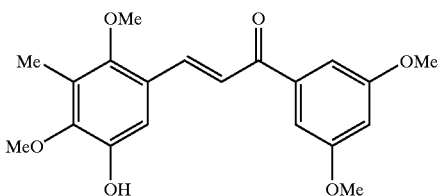

Isomers, Salts, Hydrates, Protected Forms, and Prodrugs

A certain compound may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r- forms; endo- and exo-forms; R-, S-, and meso-forms; D- and L-forms; (+) and (−) forms; keto- and enol-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms"). Note that specifically excluded from the terms "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. However, a reference to a class of structures may well include structurally isomeric forms falling within that class (e.g., C$_{1-6}$alkyl includes n-propyl and iso-propyl; butyl includes n-, iso-, sec-, and tert-butyl; methoxyphenyl includes ortho-, meta-, and para-methoxyphenyl).

Unless otherwise specified, a reference to a particular compound includes all such isomeric forms, including racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein in a known manner.

As noted above, the compounds of the present invention are all of the "E" (entgegen) or "trans" form, that is, the (optionally substituted) 4-methoxy-phenyl group (styryl phenyl group) and the 3,5-dimethoxybenzoyl group (acyl phenyl group) are positioned "trans" with respect to one another on the carbon-carbon double bond of the prop-1-ene backbone.

It may be convenient or desirable to prepare, purify, and/or handle a corresponding salt of the active compound, for example, a pharmaceutically-acceptable salt. Examples of pharmaceutically acceptable salts are discussed in Berge et al., 1977.

For example, if the compound is anionic, or has a functional group which may be anionic (e.g., —COOH may be —COO$^-$; —OSO$_3$H may be —OSO$_3^-$; —OP(=O)(OH)$_2$ may be —OP(=O)(OH)O$^-$ or —OP(=O)(O$^-$)$_2$), then a salt may be formed with a suitable cation.

Examples of suitable inorganic cations include, but are not limited to, alkali metal ions such as Na+ and K+, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, ethylenediamine, ethanolamine, diethanolamine, piperazine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, anions from the following organic acids: acetic, trifluoroacetic, propionic, isobutyric, succinic, gycolic, suberic, sebacic, stearic, caprylic, lactic, malic, tartaric, citric, ascorbic, maleic, hydroxymaleic, phenylacetic, glutamic, benzoic, chlorobenzoic, methylbenzoic, dinitrobenzoic, phthalic, salicylic, sulfanilic, 2-acetyoxybenzoic, fumaric, benzenesulfonic, toluenesulfonic, methanesulfonic, ethane disulfonic, oxalic, isethionic, and valeric.

It may be convenient or desirable to prepare, purify, and/or handle a corresponding hydrate of the active compound, for example, as the mono-hydrate, the di-hydrate, the tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group and a blocked or blocking group).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. For example, the ketone group of the present compounds may be protected in the form of a Schiff Base, by condenation with a suitable amine, or as an oxime, by reaction with hydroxylamine.

It may be convenient or desirable to prepare, purify, and/or handle the active compound in the form of a prodrug. The term "prodrug," as used herein, pertains to a compound which, when metabolised, yields the desired active compound. Typically, the prodrug is inactive, or less active than the active compound, but may provide advantageous handling, administration, or metabolic properties. For example, some prodrugs are esters of the active compound; during metabolism, the ester group is cleaved to yield the active drug. Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Synthesis

The compounds of the present invention may be prepared, for example, by Aldol condensation of the corresponding carbonyl compounds A and B, as illustrated below in Scheme 1.

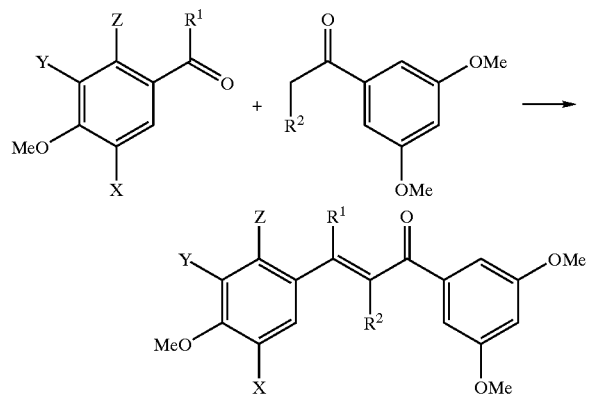

For example, compound III may be prepared by stirring a solution of 3-hydroxy-4-methoxybenzaldehyde and 3,5-dimethoxyacetophenone in methanol (as solvent) with added aqueous sodium hydroxide solution (as base catalyst) for 18 hours at ambient temperature. The mixture is acidified with hydrochloric acid to give the product which is then collected by filtration. The reaction is illustrated below in Scheme 2.

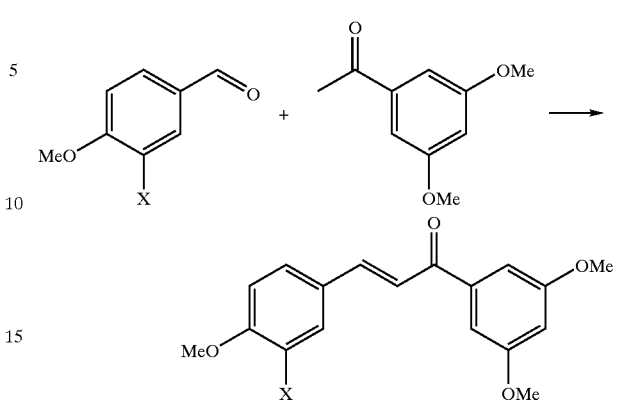

Additional methods for the preparation of compounds of the present invention, for example, where $R^1$ and/or $R^2$ are other than hydrogen, are described in the Examples below.

Compounds for which X is —OC(=O)R$^3$, —OS(=O)$_2$OH, or —OP(=O)(OH)$_2$ may be prepared from their hydroxy analogs (where X is —OH) by reaction with an organic acid (i.e., R$^3$COOH) or an inorganic acid (i.e., sulfuric acid, H$_2$SO$_4$; phosphoric acid, H$_3$PO$_4$).

The groups —OS(=O)$_2$OH and —OP(=O)(OH)$_2$ may be present as such, in their free acid form, or they may be present as a salt or ester thereof, as discussed above. For example, the group —OS(=O)$_2$OH may be present as —OS(=O)$_2$O$^-$ M$^+$, wherein M$^+$ is a suitable cation. Similarly, the group —OP(=O)(OH)$_2$ may be present as —OP(=O)(OH)O$^-$ M$^+$ or —OP(=O)(O$^-$)$_2$(M$^+$)$_2$, wherein M$^+$ is a suitable cation. Examples of suitable cations are discussed above. In one embodiment, the group —OP(=O)(OH)$_2$ is present as the disodium salt, —OP(=O)(O$^-$)$_2$(Na$^+$)$_2$. Other salts and esters are described in Pettit et al, 1995.

Active Compounds and Prodrugs of Active Compounds

As demonstrated in the examples below, the compounds of the present invention are highly potent antiproliferative agents, and/or are prodrugs for highly potent antiproliferative agents.

Compounds of the present invention which exhibit low or moderate intrinsic activity may act as prodrugs, and be metabolically activated to generate more potent compounds of the present invention. This is especially useful in cancer therapy where metabolic activation can be achieved by an enzyme that is expressed in tumours. For example, the cytochrome P-450 enzyme CYP1B1 has been shown to be specifically expressed in tumour cells, but is not found in the corresponding normal tissues. This enzyme is found to be expressed in a variety of tumours, such as brain, breast, colon, stomach, ovarian and prostate cancers (Murray et al, 1997).

For example, compound III is a very potent anticancer agent with activity against a number of human tumour cells lines. Compound II, has low intrinsic activity, but is metabolised by CYP1B1 through an aromatic hydroxylation reaction to generate the potent anticancer agent compound III. In this way, compound II may act as a non-toxic prodrug which is activated by CYP1B1 to generate the highly potent anticancer compound of formula III, as illustrated in Scheme 3, below.

Scheme 3

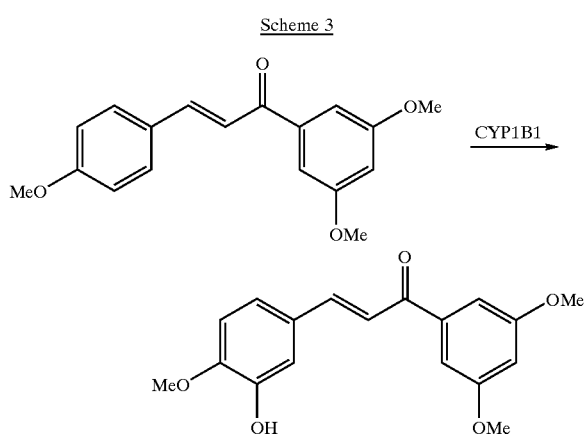

In such cases, the prodrug is useful as a selective anti-cancer agent with low intrinsic toxicity. Furthermore, pro-drugs with low intrinsic cytotoxicity, which are only activated upon entering tumour cells containing the CYP1B1enzyme, are not only useful for treating cancer, but also as a prophylactic, in cancer prevention (i.e., as a cancer preventative agent).

Furthermore, the hydroxylated metabolite, compound III, exhibits much greater fluorescence than the prodrug, compound II, and this property may be exploited in the diagnosis of cancer, by detecting and/or measuring the formation of the hydroxylated metabolite.

Thus, one aspect of the present invention pertains to a method of diagnosis of a patient for the presence of tumour cells expressing the CYP1B1 enzyme, comprising:

(a) administering to the patient a non-hydroxylated pro-drug as described herein, wherein X is —H (e.g., compound II);

(b) determining the amount of the corresponding hydroxylated metabolite, wherein X is —OH (e.g., compound III) which is subsequently produced; and, (c) correlating the amount with the presence or absence of the tumour cells in the patient.

Use of Compounds

The present invention provides active compounds, specifically, active substituted-1-(4-methoxyphenyl)-3-(3,5-dimethoxyphenyl) prop-1-en-3-ones, which regulate cell proliferation, as well as methods of regulating cell proliferation, comprising contacting a cell with an effective amount of an active compound, whether in vitro or in vivo.

The term "active," as used herein, pertains to compounds which are capable of regulating cell proliferation, and specifically includes both compounds with intrinsic activity (drugs) as well as prodrugs of such compounds, which prodrugs may themselves exhibit little or no intrinsic activity.

One of ordinary skill in the art is readily able to determine whether or not a candidate compound is active, that is, regulates cell proliferation for any particular cell line. For example, one assay which may conveniently be used to assess the proliferation regulation offered by a particular compound is described in the examples below.

For example, a sample of cells (e.g., from a tumour) may be grown in vitro and a candidate compound brought into contact with the cells, and the effect of the compound on those cells observed. As examples of "effect," the morpho-logical status of the cells may be determined (e.g., alive or dead), or the expression levels of genes associated with cell cycle regulation determined. Where the candidate compound is found to exert an influence on the cells, this may be used as a prognostic or diagnostic marker of the efficacy of the compound in methods of treating a patient carrying the tumour or a tumour of the same cellular type.

Thus, in one aspect, the present invention provides anti-proliferative agents. The term "antiproliferative agent" as used herein, pertain to a compound which treats a proliferative condition (i.e., a compound which is useful in the treatment of a proliferative condition).

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

Antiproliferative compounds of the present invention have application in the treatment of cancer, and so the present invention further provides anticancer agents. The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

The present invention also provides active compounds, specifically, active substituted-1-(4-methoxyphenyl)-3-(3,5-dimethoxyphenyl) prop-1-en-3-ones, which are useful in the treatment of inflammatory conditions. For example, such compounds have growth down-regulatory effects on splenocytes. Examples of inflammaotry conditions include, but are not limited to, rheumatoid arthritis, rheumatic fever, osteoarthritis, inflammatory bowel disease, psoriasis, and bronchial asthma.

The invention further provides active compounds for use in a method of treatment of the human or animal body. Such a method may comprise administering to such a subject a therapeutically-effective amount of an active compound, preferably in the form of a pharmaceutical composition.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio.

The invention further provides the use of an active compound for the manufacture of a medicament, for example, for the treatment of a proliferative condition or an inflammatory condition, as discussed above.

The invention further provides a method of treatment of the human or animal body, the method comprising administering to a subject in need of treatment a therapeutically-effective amount of an active compound, preferably in the form of a pharmaceutical composition.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other antiproliferative agents, other antiinflammatory agents, etc.

Administration

The active compound or pharmaceutical composition comprising the active compound may be administered to a subject by any convenient route of administration, whether systemically/peripherally or at the site of desired action, including but not limited to, oral (e.g., by ingestion); topical (including transdermal, intranasal, ocular, buccal, and sublingual); pulmonary (e.g., by inhalation therapy using, for example, an aerosol); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal.

The subject may be a eukaryote, an animal, a vertebrate animal, a mammal, a rodent (e.g., a guinea pig, a hamster, a rat, a mouse), murine (e.g., a mouse), a simian (e.g., a chimpanzee), or a human.

Formulations

While it is possible for the active ingredient to be administered alone, it is preferable to present it as a pharmaceutical composition (e.g., formulation) comprising at least one active ingredient, as defined above, together with one or more pharmaceutically acceptable carriers, excipients, diluents, buffers, adjuvants, stabilisers, or other materials well known to those skilled in the art and optionally other therapeutic agents.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations may be in the form of liquids, solutions, suspensions, emulsions, tablets, losenges, granules, powders, capsules, cachets, pills, ampoules, suppositories, pessaries, ointments, gels, pastes, creams, sprays, foams, lotions, oils, boluses, electuaries, or aerosols.

Formulations suitable for oral administration (e.g., by ingestion) may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose), surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active ingredients and optionally one or more excipients or diluents.

Formulations suitable for topical administration in the mouth include losenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for topical administration to the eye also include eye drops wherein the active ingredient is dissolved or suspended in a suitable carrier, especially an aqueous solvent for the active ingredient.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active ingredient.

Formulations suitable for topical administration via the skin include ointments, creams, and emulsions. When formulated in an ointment, the active ingredient may optionally be employed with either a paraffinic or a water-miscible ointment base. Alternatively, the active ingredients may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at lease one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active ingredient in the solution is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect.

Administration in vivo can be effected in one dose, continuously or intermittently throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 0.01 to about 100 mg per kilogram body weight of the subject per day. Where the active ingredient is a salt, an ester, prodrug, or the like, the amount administered is calculated on the basis the parent compound and so the actual weight to be used is increased proportionately.

EXAMPLES

The following are examples are provided solely to illustrate the present invention and are not intended to limit the scope of the invention, as described herein. Unless otherwise specified, all reagents were purchased from Sigma-Aldrich, Dorset, UK.

Example 1

(E)-1-(4-Methoxyphenyl)-3-(3,5-dimethoxyphenyl) prop-1-en-3-one (Compound II, DMU-120)

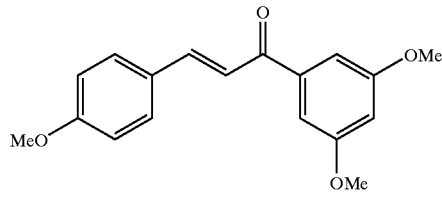

To a stirred solution of 4-methoxybenzaldehyde (0.709 g, 5.21 mmol) and 3,5-dimethoxyacetophenone (0.939 g, 5.21 mmol) in methanol (20 ml) was added a 50% w/v solution of aqueous NaOH (4 ml). The mixture was stirred for 1 h at room temperature. The mixture was acidified (conc. HCl) and the resultant precipitate collected by filtration. Recrystallisation from methanol afforded the product as fine pale yellow crystals (1.05 g, 68%).

Mp 87–88° C.; $^1$H NMR δ (CDCl$_3$) 3.85 (6H, s, OCH$_3$), 3.86 (3H, s, OCH$_3$), 6.65 (1H, s), 6.95 (2H, d), 7.15 (2H, s), 7.35 (1H, d), 7.60 (2H, d), 7.75 (1H, d); $^{13}$C NMR d (CDCl$_3$)

55.42, 55.62, 104.78, 106.25, 114.41, 119.75, 127.56, 130.26, 140.51, 144.84, 160.83, 161.69, 190.18; MS (rel intensity) m/z 299 ([M+H]⁺, 100%); IR $\nu_{max}$ (KBr)/cm⁻¹ 1650 (C=O).

Example 2

(E)-1-(3-Hydroxy-4-methoxyphenyl)-3-(3,5-dimethoxyphenyl)prop-1-en-3-one (Compound III, DMU-153)

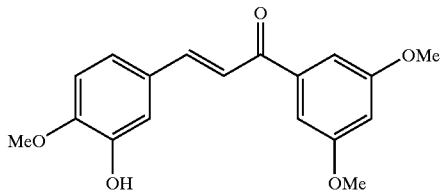

To a stirred solution of 3-hydroxy-4-methoxybenzaldehyde (0.76 g, 5 mmol) and 3,5-dimethoxyacetophenone (0.90 g, 5 mmol) in methanol (10 ml) was added aqueous NaOH (4 ml, 50% w/v) and the mixture stirred for 18 h at room temperature. The mixture was acidified (conc. HCl, 6 ml) and the resultant precipitate collected by filtration. The crude solid was dissolved in chloroform, washed with water (2×50 ml), and dried over anhydrous sodium sulfate. Evaporation and recrystallisation from methanol afforded the product as a pale yellow solid (0.75 g, 48%).

Mp 129° C.; IR $\nu_{max}$ (KBr)/cm⁻¹ 1660 (C=O). ¹H NMR δ (CDCl₃) 3.86 (6H, s, OCH₃), 3.93 (3H, s, OCH₃), 5.73 (1H, s, OH), 6.66 (1H, t, J=2.3 Hz, H-4'), 6.65 (1H, d, J=8.35 Hz, H-5), 7.13 (3H, m, ArH), 7.27 (1H, d, J=2.1 Hz, H-2), 7.33 (1H, d, J=15.6 Hz, CH), 7.73 (1H, d, J=15.6 Hz, CHCO); ¹³C NMR d (CDCl₃) 55.67, 56.07, 105.03, 106.28, 110.62, 113.09, 120.31, 122.80, 128.56, 140.50, 144.97, 145.96, 148.91, 160.91, 190.15; MS (rel intensity) m/z 315 ([M+H]⁺, 100%); Anal. Calcd (C₁₈H₁₈O₅.0.5H₂O): C, 66.86; H, 5.92. Found C, 66.83; H, 5.91.

Example 3

(E)-1-(2,4-dimethoxyphenyl)-3-(3,5-dimethoxyphenyl)prop-1-en-3-one (Compound IV, DMU-162)

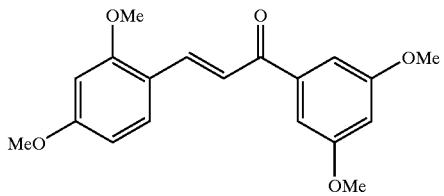

A mixture of 2,4-dimethoxybenzaldehyde (1.89 g, 0.011 mol), 3,5-dimethoxyacetophenone (2.05 g, 0.011 mol) and 50% w/v of aqueous sodium hydroxide (9.1 ml, 0.11 mol) in methanol (20 ml) were stirred at room temperature for 1 hour. The yellow solid that precipitated was filtered and sequentially washed with cold methanol and ether and finally dried in a vacuum dessicator. Purification by recrystallisation from methanol gave 2.7 g (73%) of the product as yellow crystals.

¹H-NMR (CDCl₃) 8.0 (d, 1H), 7.5 (d, 1H), 7.4 (d, 1H), 7.1 (d, 2H), 6.65 (m, 1H), 6.5 (dd, 1H), 6.4 (d, 1H), 3.85 (s, 3H), 3.8 (s, 3H), 3.75 (s, 6H). ¹³C NMR (CDCl₃) 190.6, 163.1, 160.8, 160.4, 140.8, 140.5, 130.8, 121.5, 120.3, 117.0, 107.5, 106.2, 105.0, 98.4, 56.6, 55.5, 54.3. Mass Spectrum m/e (M+1) 329.

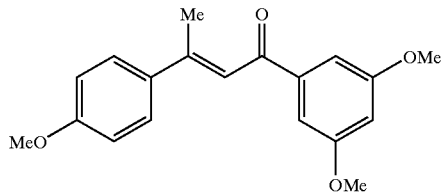

3,5-Dimethoxyacetophenone trimethylsilyl enol ether was prepared by reaction of 3,5-dimethoxyacetophenone with trimethylsilyltrifluoromethanesulfonate in the presence of trimethylamine base, in dichloromethane as solvent. A dichloromethane solution was prepared containing 4-methoxyacetophenone (0.3 g, 2 mmol), 3,5-dimethoxyacetophenone trimethylsilyl enol ether (2 mmol) and triethylamine (0.55 ml, 4 mmol). To this solution was added trifluoroacetic anhydride (0.28 ml, 2 mmol), followed by titanium tetrachloride (0.38 g, 2 mmol), and the resulting mixture stirred at ambient temperature for 4 hours. The product was purified by column chromatography (SiO₂, petroleum:ether (40:60 v/v) with an increasing gradient elution of ethyl acetate, 0–25%) to furnish the product as a colourless oil. Mass Spectrum m/e (M+1) 313.

Example 5

(E)-1-(4-methoxyphenyl)-2-methyl-3-(3,5-dimethoxyphenyl)prop-1-en-3-one (Compound VI, DMU-428)

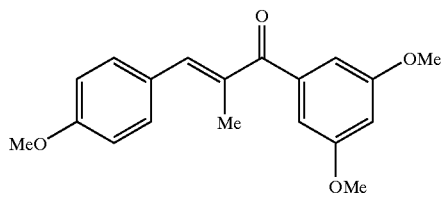

(a) 3,5-Dimethoxybenzaldehyde (1 g, 6 mmol), in dry tetrahydrofuran (20 ml), was added over 15 min to ethylmagnesium bromide (7.23 ml (1.0 M solution in tetrahydrofuran), 7.2 mmol) in dry tetrahydrofuran (10 ml) at 0° C., under nitrogen. After refluxing the mixture for 18 hours, a grey solution was obtained. The reaction was then quenched by adding ice and 1 M hydrochloric acid (20 ml) dropwise and the aqueous phase was extracted with ether (3×25 ml), the combined organic layers were dried over anhydrous magnesium sulfate and reduced in vacuo. Purification by column chromatography (SiO₂, petroleum:ether (40:60 v/v) with an increasing gradient of ethyl acetate, 0–20%) gave 0.85 g (72%) of the alcohol as a yellow oil.

(b) To a stirred solution of dimethylsulfoxide (0.694 ml, 9.8 mmol) in dry dichloromethane (5 ml) at −78° C. was added, over 15 min, oxalyl chloride (0.424 ml, 4.9 mmol) under nitrogen. The solution was stirred for 15 min at −78° C. until the evolution of gas stopped, then a solution of the alcohol (0.85 g, 4.3 mmol) in dichloromethane (5 ml) was added over 15 min. The mixture was stirred at −78° C. for a further 30 min before triethylamine (3.0 ml, 21.6 mmol) was added over 10 min, this was stirred for a further 5 min at −78° C. and then allowed to warm up to room temperature and left for 2 hours. The mixture was then diluted with dichloromethane (20 ml) and the organic layer was sequentially washed with 1 M hydrochloric acid (2×15 ml), water (2×15 ml), dried over magnesium sulfate, and reduced in vacuo. Purification by column chromatography (SiO$_2$, petroleum:ether (40:60 v/v) with an increasing gradient of ethyl acetate, 0–25%)) gave 0.68 g (80%) of the ketone as a yellow solid.

(c) A mixture of the ketone (1 g, 5.2 mmol), 4-methoxybenzaldehyde (0.612 ml, 5.1 mmol), piperidine (1.14 ml, 11.5 mmol) and glacial acetic acid (0569 ml, 9.9 mmol) in dry ethanol (100 ml) were heated under reflux and water was removed from the reaction by soxhlet extraction over 4A molecular sieves for 50 hours. The solvent was removed in vacuo and the residue was purified by column chromatography (SiO$_2$, petroleum:ether (40:60 v/v) with an increasing gradient of ethyl acetate (0–25%)). Further purification by recrystallisation from methanol gave 0.390 g (24%) of the product as pale yellow crystals.

$^1$H-NMR (CDCl$_3$) 7.4 (d, 2H), 7.2 (d, 1H), 6.9 (d, 2H), 6.8 (d, 2H), 6.6 (t, 1H), 3.9 (s, 3H), 3.85 (s, 3H), 2.3 (s, 3H). $^{13}$C NMR (CDCl$_3$) 188.9, 160.5, 144.0, 141.6, 140.9, 134.7, 132.9, 130.5, 128.4, 115.3, 112.7, 108.5, 106.0, 104.9, 102.5, 56.7, 54.4. Mass Spectrum m/e (M+1) 313.

Example 6

(E)-1-(3-Hydroxy-4-methoxyphenyl)-3-(3,5-dimethoxyphenyl)prop-1-en-3-one oxime (Compound VII, DMU-153)

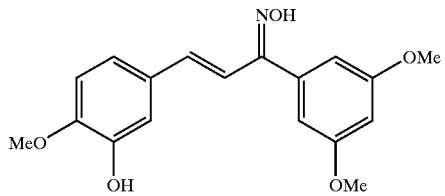

To a solution of hydroxylamine hydrochloride (0.5 g) in water (2 ml) was added an aqueous solution of sodium hydroxide (10% w/v, 2 ml), followed by the addition of a solution of Compound III (DMU-153, 0.1 g) dissolved in ethanol (2 ml). The mixture was heated under reflux for 30 min, and then cooled in an ice bath to give the product as a white crystalline solid.

Example 7

(E)-1-(3-acetoxy-4-methoxyphenyl)-3-(3,5-dimethoxyphenyl)prop-1-en-one (Compound VIII, DMU-170)

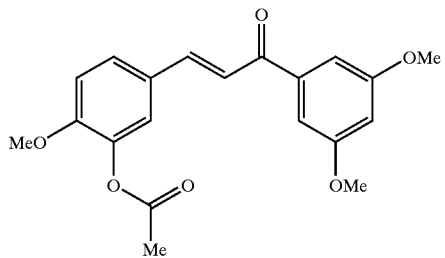

To a stirred solution of Compound III (DMU-153) (0.314 g, 1 mmol) in chloroform (20 ml) was added N-ethyldiisopropylamine (0.171 ml, 1 mmol) and acetyl chloride (0.711 ml, 10 mmol) and the mixture stirred for 24 hours at room temperature. The mixture was diluted with water (20 ml) and the organic phase separated and dried over anhydrous sodium sulfate. Evaporation and recrystallisation from methanol afforded the product as a cream solid (0.30 g, 84%).

$^1$H NMR δ (CDCl$_3$) 2.34 (3H, s, OCOCH$_3$), 3.86 (6H, s, OCH$_3$), 3.88 (3H, s, OCH$_3$), 6.66 (1H, t, J=2.3 Hz, H-4'), 6.98 (1H, d, J=8.5 Hz, H-5), 7.12 (2H, d, J=2.3 Hz, H-2',6'), 7.30 (1H, d, J=15.6 Hz, CH), 7.38 (1H, d, J=2.2 Hz, H-2), 7.46 (1H, dd, J=2.2, 8.5 Hz, H-6), 7.73 (1H, d, J=15.6 Hz, CHCO); $^{13}$C NMR δ (CDCl$_3$) 20.56, 55.61, 56.02, 104.96, 106.29, 112.38, 120.77, 122.06, 128.04, 128.39, 140.13, 140.34, 143.78, 153.17, 160.89, 168.75, 189.85; MS m/z 357 (M+1); IR (KBr) cm$^{-1}$ 1780, 1650, 1590; Anal. Calcd (C$_{20}$H$_{20}$O$_6$): C, 67.41; H, 5.66. Found C, 67.13; H, 5.69.

Example 8

Anticancer Activity

Compound III was tested against a number of human tumour cell lines and found to be a very potent anticancer agent. In particular it has highly potent anticancer activity against human tumours such as breast tumours, colon tumours, and lung tumours. The results are summarised in Table 1.

TABLE 1

Anticancer Activity of Compound III
(results expressed as dose required for 50%
inhibition of tumour cell growth, IC50/μM)

| Tumour Cells | Compound III (DMU-153) IC50/μM |
|---|---|
| Breast MCF-7 | 0.00065 |
| Colon HCT-116 | 0.00008 |
| Lung A-549 | 0.08 |

Compound IV (DMU-428) was tested against Breast MCF-7 tumour cells, and also found to be a very potent anticancer agent. The results are summarised in Table 2.

TABLE 2

Anticancer Activity of Compound IV
(results expressed as dose required for 50%
inhibition of tumour cell growth, IC50/μM)

| Tumour Cells | Compound IV (DMU-428) IC50/μM |
|---|---|
| Breast MCF-7 | 0.0001 |

The human tumour cell lines were the breast cancer cell line MCF-7, the colon cancer cell line HCT-116, and the lung cancer cell line A-549. The MTT assay was used, which exploits the ability of living cells to metabolise the water soluble tetrazolium salt 3-[4,5-dimethylthiazol-2yl-2,5-diphenyl tetrazolium bromide (MTT) into a water insoluble formazan precipitate (Carmichael et al, 1987). The purple precipitate can then be dissolved in an organic solvent and the optical density determined as a measure of cell survival. Compounds were tested concurrently for a true comparison.

The compound under study was dissolved in DMSO to yield a 10 mM stock solution. The final concentration of DMSO (1% max) was found to have minimal effects on the assay result. Cells were seeded into sterile flat-bottomed 96-well plates at a known initial seeding density (MCF-7

1.5×10E3, HCT-116 1×10E3, A549 2×10E3). The cells were plated in RPMI 1640 medium supplemented with 10% heat-inactivated Foetal Calf Serum solution. The plates were then incubated for 24 h at 37° C., 5% $CO_2$ to allow cell adherence. 20 µl of the appropriate drug dilution (from serial dilutions in medium from 10 mM stock) was added to the wells (to give a final well volume of 200 µl). Plates were returned to the incubator for 96 h, and then 50 µl of MTT was added to each well. After a further 4 h incubation, the medium and any unconverted MTT was aspirated from the wells and the formazan precipitate dissolved by the addition of 100 µl of DMSO and several minutes agitation. The absorbance at $A_{450}$ was then recorded on a plate reader, and the results expressed as a % survival of DMSO treated controls. From this data was calculated the concentration at which 50% cytotoxicity is observed ($IC_{50}$).

Compound III exhibits very potent activity against the breast cancer cell line MCF-7 with an $IC_{50}$ of 0.00065 µM. The activity against the colon tumour cell line HCT-116 is even more impressive with an extremely potent activity of 0.00008 µM (0.08 nM). The activity against the lung cancer cell line A-549 is also of useful potency at 0.08 µM, since this is a cell line derived from a non-small cell lung carcinoma (NSCLC) which is refractory to commonly used chemotherapeutic agents.

Compound IV is even more potent than Compound III against the breast cancer cell line MCF-7, with an $IC_{50}$ of 0.0001 µM.

Example 9

Compounds as Prodrugs

Compound II is metabolised by the cytochrome P-450 enzyme CYP1B1 through an aromatic hydroxylation reaction to generate compound III, and thus compound II acts a prodrug which is activated by CYP1B1 to generate the highly potent anticancer compound III.

A microsomal preparation of human tumour tissue expressing the CYP1B1 enzyme was prepared essentially as described by the method of Barrie et al., 1989. The experiment was carried out at 37° C., under yellow light. An array of 1.5 ml centrifuge tubes were set up in a water bath shaker-under aerobic conditions. To each tube was then added 500 µl of pH 7.6 buffer (0.1 M $NaK_2PO_4$), followed by NADPH (5 µl of a 25 mM stock solution). The microsomal preparation (80 µl) was then added and the tubes preincubated for 5 min at 37° C.

The prodrug substrate, compound II, was then added (10 µl of a 5 mM stock solution) and incubated for 1 h at 37° C. After 1 h the tubes were transferred to an ice/water cooling bath (0° C.). The tubes were then centrifuged at 15,000 rpm for 30 min. A sample of the supernatant (100 µl) was then taken and analysed by HPLC. HPLC conditions: Spherisorb C18 (25 cm×4.6 mm id), used without guard column. Flow rate 1 ml/min. Eluent 75% 0.1 M $KH_2PO_4$ and 25% acetonitrile.

The hydroxylated metabolite, compound III, was detected by HPLC, and confirmed by comparison with the authentic hydroxylated synthetic compound III. More specifically, compound II, (E)-1-(4-Methoxyphenyl)-3-(3,5-dimethoxyphenyl)prop-1-en-3-one, was converted to the hydroxylated metabolite compound III, (E)-1-(3-Hydroxy-4-methoxyphenyl)-3-(3,5-dimethoxyphenyl)prop-1-en-3-one.

The anticancer activity of Compound II, and the resulting CYP1B1 hydroxylated metabolite compound III, were determined using the methods described above. The results are summarised in Table 3.

TABLE 3

Anticancer Activity of Compound II and its CYP1B1 Hydroxylated Metabolite Compound III (results expressed as dose required for 50% growth inhibition, IC50/µM)

| Tumour | Compound II (DMU-120) IC50/µM | Compound III (DMU-153) IC50/µM | Selectivity Factor (Prodrug/ Metabolite) |
|---|---|---|---|
| Breast MCF-7 | 0.69 | 0.00065 | 1100 |
| Colon HCT-116 | 1.2 | 0.00008 | 15000 |
| Lung A-549 | 6.6 | 0.08 | 80 |

Example 10

Anti-Inflammatory Activity

The compounds of the present invention also show growth down-regulatory effects on splenocytes. Since splenocytes are involved in inflammation, these compounds are also useful as anti-inflammatory agents.

The anti-inflammatory effects of Compound II (DMU-120) were examined (in triplicate) using a splenocyte anti-proliferation assay.

The splenocyte anti-proliferation assay has been developed to identify compounds that have useful anti-inflammatory properties for the treatment of auto-inflammatory diseases such as rheumatoid arthritis. See, for example, Yamashita et al., 1994. This well known assay is described in detail in, for example, Mosmann, 1983. In this assay, splenocyte proliferation is stimulated by the inflammatory response inducer conconavilin A (Con A). Cell proliferation is monitored by detecting radiation (counts per minute, cpm) from a radio label (tritiated thymidine) which is incorporated only into proliferating cells.

The results are summarised in FIG. 1. The compound was assayed as a solution in dimethylsulfoxide (DMSO) as solvent. The solvent control is also shown for comparison. Other controls are also shown. "ConA" denotes the signal (cpm) detected for a control where cell proliferation is stimulated by ConA in the absence of a test compound. "Med" denotes the signal (cpm) detected for the cell culture medium alone. "Bkg" denotes the background radiation level (cpm).

Compounds that exhibit anti-inflammatory effects at a concentration of less than 10 µM are considered to be useful therapeutic agents. Compound II clearly shows anti-inflammatory effects on splenocyte proliferation at concentrations less than 10 µM and therefore exhibits useful anti-inflammatory properties.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure.

Akihiko, 1986, Japanese Patent Publication No. 61-076433, published Apr. 18, 1986.

Barrie et al., 1989, *J. Steroid Biochem.*, Vol. 6, pp. 1191–1195.

Berge et al., 1977, "Pharmaceutically Acceptable Salts," *J. Pharm. Sci.*, Vol. 66, pp. 1–19.
Berryman et al., 1995, published International Patent Application, publication number WO 95/05376, published Feb. 23, 1995.
Berryman et al., 1997, U.S. Pat. No. 5,691,373, issued Nov. 25, 1997.
Carmichael et al., 1987, "Title," *Cancer Research*, Vol. 47, p. 936.
Ducki et al., 1998, "Potent Antimitotic and Cell growth Inhibitory Properties of Substituted Chalcones," BioMed. Chem. Lett., Vol. 8, pp. 1051–1056.
Hiromitsu, 1996, Japanese Patent Publication No 08-188546, published Jul. 23, 1996.
Mosmann, T., 1983, *Journal of Immunological Methods*, Vol. 65, pp. 55–63.
Murray et al., 1997, "Title," *Cancer Research*, Vol. 57, p. 3026.
Pettit et al, 1995, "Synthesis of Combretastatin prodrugs," *Anticancer Drug Design*, Vol. 10, pp. 299–309.
Yamashida, D. S., et al, 1994, *Bioorg. Med. Chem. Lett.*, Vol. 4, pp. 325–328.

What is claimed is:

1. A compound of the formula:

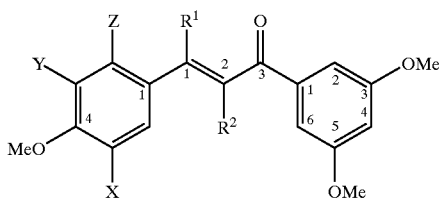

I wherein:
X is —H, —OH, —OC(=O)R$^3$, —OS(=O)$_2$OH, or —OP(=O)(OH)$_2$;
Y is —H or a C$_{1-4}$alkyl group;
Z is —H or —OCH$_3$;
R$^1$ is —H, a C$_{1-4}$alkyl group, or C$_{1-4}$fluoroalkyl group;
R$^2$ is —H, a C$_{1-4}$alkyl group, or C$_{1-4}$fluoroalkyl group; and,
R$^3$ is —H, a C$_{1-6}$alkyl group, a C$_{3-20}$heterocyclyl group, or a C$_{5-20}$aryl group;
or a pharmaceutically acceptable salt, ester, or protected form thereof;
with the proviso that X, Y, Z, R$^1$, and R$^2$ are not all —H.

2. A compound according to claim 1, wherein X is —H.
3. A compound according to claim 1, wherein X is —OH, —OC(=O)R$^3$, —OS(=O)$_2$OH, or —OP(=O)(OH)$_2$.
4. A compound according to claim 1, wherein X is —OH.
5. A compound according to claim 1 wherein Y is —H, —CH$_3$, or —CH$_2$CH$_3$.
6. A compound according to claim 2, wherein Y is —H, —CH$_3$, or —CH$_2$CH$_3$.
7. A compound according to claim 4, wherein Y is —H, —CH$_3$, or —CH$_2$CH$_3$.
8. A compound according to claim 1, wherein Y is —H.
9. A compound according to claim 2, wherein Y is —H.
10. A compound according to claim 4, wherein Y is —H.
11. A compound according to claim 1, wherein Z is —H.
12. A compound according to claim 2, wherein Z is —H.
13. A compound according to claim 4, wherein Y is —H.
14. A compound according to claim 5, wherein Z is —H.
15. A compound according to claim 6, wherein Z is —H.
16. A compound according to claim 7, wherein Z is —H.
17. A compound according to claim 8, wherein Z is —H.
18. A compound according to claim 9, wherein Z is —H.
19. A compound according to claim 10, wherein Z is —H.
20. A compound according to claim 1, wherein Z is —OCH$_3$.
21. A compound according to claim 2, wherein Z is —OCH$_3$.
22. A compound according to claim 4, wherein Z is —OCH$_3$.
23. A compound according to claim 5, wherein Z is —OCH$_3$.
24. A compound according to claim 6, wherein Z is —OCH$_3$.
25. A compound according to claim 7, wherein Z is —OCH$_3$.
26. A compound according to claim 8, wherein Z is —OCH$_3$.
27. A compound according to claim 9, wherein Z is —OCH$_3$.
28. A compound according to claim 10, wherein Z is —OCH$_3$.
29. A compound according to claim 1, wherein R$^1$ and R$^2$ are independently —H, —CH$_3$, —CH$_2$CH$_3$, —CF$_3$, —CH$_2$CF$_3$, or —CF$_2$CF$_3$.
30. A compound according to claim 1, wherein both R$^1$ and R$^2$ are —H.
31. A compound according to claim 1, wherein R$^3$ is —CH$_3$, —CH$_2$CH$_3$, —C(CH$_3$)$_3$, or -Ph.
32. A compound according to claim 1, having the formula:

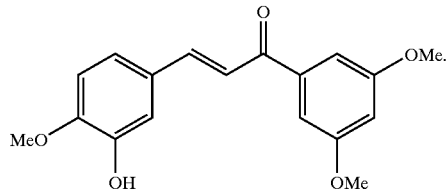

III

33. A compound according to claim 1, having the formula:

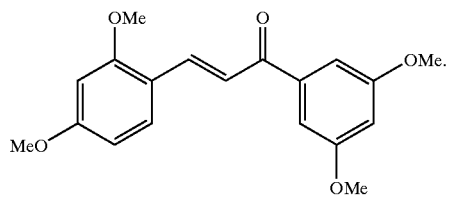

IV

34. A compound according to claim 1, having the formula:

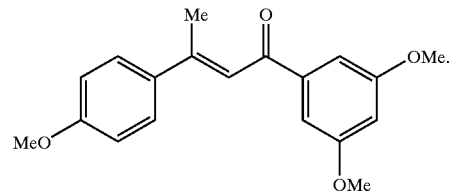

V

35. A compound according to claim 1, having the formula:

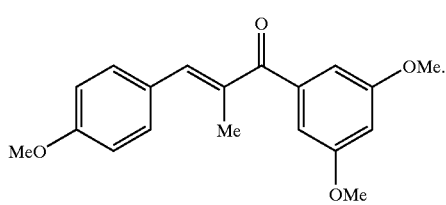
VI

36. A compound according to claim 1, having the formula:

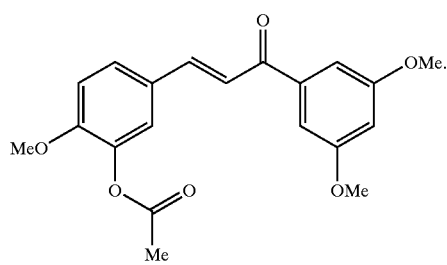
VIII

37. A compound according to claim 1, having the formula:

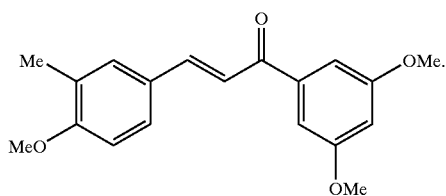
IX

38. A compound according to claim 1, having the formula:

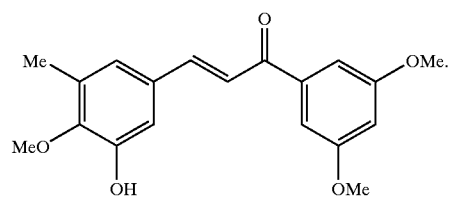
X

39. A compound according to claim 1, having the formula:

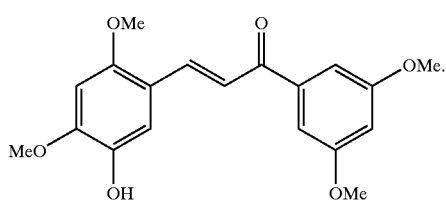
XI

40. A compound according to claim 1, having the formula:

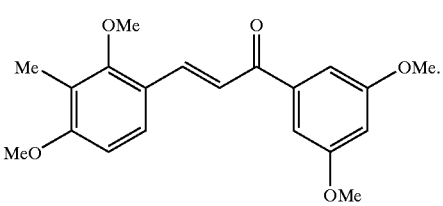
XII

41. A compound according to claim 1, having the formula:

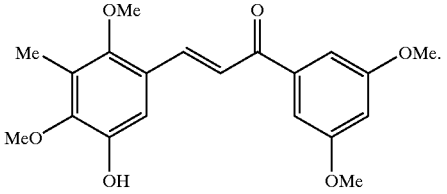
XIII

42. A composition comprising a compound according to claim 1 and a pharmaceutically acceptable carrier.

43. A method of treating a proliferative condition in a patient comprising administering to said patient a therapeutically-effective amount of a compound having the formula:

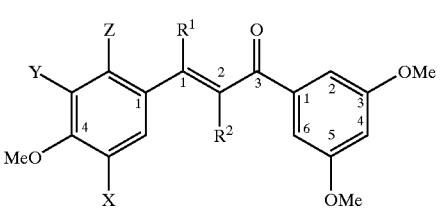
I wherein:
$X$ is —H, —OH, —OC(=O)R$^3$, —OS(=O)$_2$OH, or —OP(=O)(OH)$_2$;
$Y$ is —H or a $C_{1-4}$alkyl group;
$Z$ is —H or —OCH$_3$;
$R^1$ is —H, a $C_{1-4}$alkyl group, or $C_{1-4}$fluoroalkyl group;
$R^2$ is —H, a $C_{1-4}$alkyl group, or $C_{1-4}$fluoroalkyl group; and,
$R^3$ is —H, a $C_{1-6}$alkyl group, a $C_{3-20}$heterocyclyl group, or a $C_{5-20}$aryl group;
or a pharmaceutically acceptable salt, ester, or protected form thereof.

44. A method according to claim 43, wherein X is —H.
45. A method according to claim 43, wherein X is —OH, —OC(=O)R$^3$, —OS(=O)$_2$OH, or —OP(=O)(OH)$_2$.
46. A method according to claim 43, wherein X is —OH.
47. A method according to claim 43, wherein Y is —H.
48. A method according to claim 44, wherein Y is —H.
49. A method according to claim 46, wherein Y is —H.
50. A method according to claim 43, wherein Z is —H.
51. A method according to claim 44, wherein Z is —H.
52. A method according to claim 46, wherein Z is —H.
53. A method according to claim 47, wherein Z is —H.

54. A method according to claim 48, wherein Z is —H.

55. A method according to claim 49, wherein Z is —H.

56. A method according to claim 43, wherein Z is —OCH$_3$.

57. A method according to claim 44, wherein Z is —OCH$_3$.

58. A method according to claim 46, wherein Z is —OCH$_3$.

59. A method according to claim 47, wherein Z is —OCH$_3$.

60. A method according to claim 48, wherein Z is —OCH$_3$.

61. A method according to claim 49, wherein Z is —OCH$_3$.

62. A method according to claim 43, wherein both R$^1$ and R$^2$ are —H.

63. A method according to claim 43, wherein both R$^3$ is —CH$_3$, —CH$_2$CH$_3$, —C(CH$_3$)$_3$, or -Ph.

64. A method according to claim 43, wherein the compound has the formula:

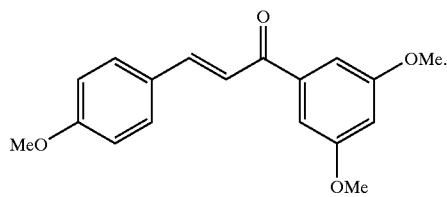

II

65. A method according to claim 43, wherein the compound has the formula:

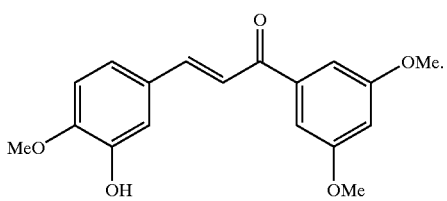

III

66. A method according to claim 43, having the formula:

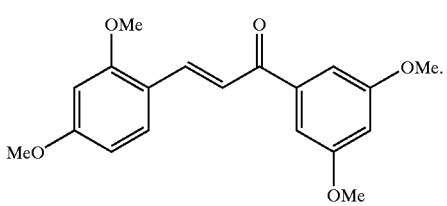

IV

67. A method according to claim 43, having the formula:

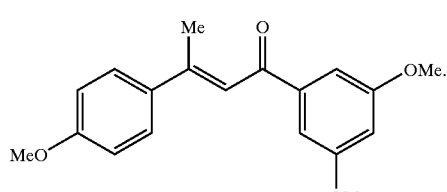

V

68. A method according to claim 43, having the formula:

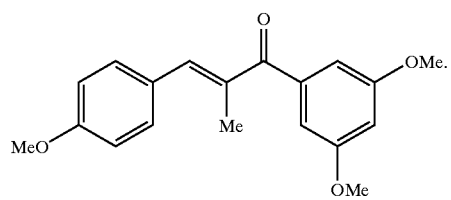

VI

69. A method according to claim 43, having the formula:

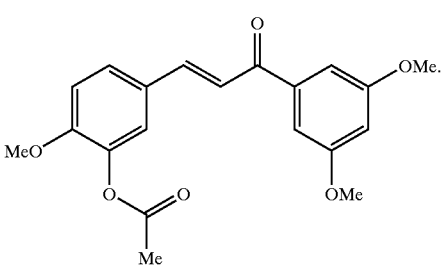

VIII

70. A method according to claim 43, having the formula:

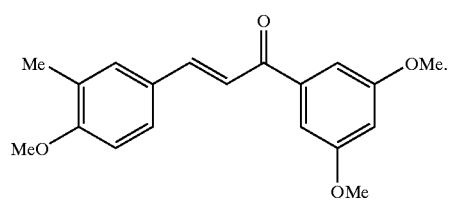

IX

71. A method according to claim 43, having the formula:

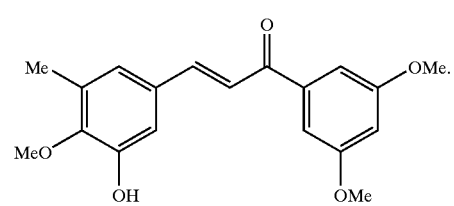

X

72. A method according to claim 43, having the formula:

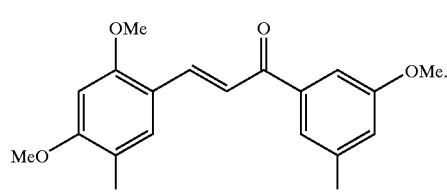

XI

73. A method according to claim 43, having the formula:

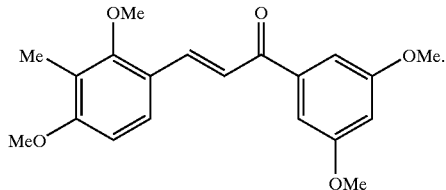

74. A method according to claim 43, having the formula:

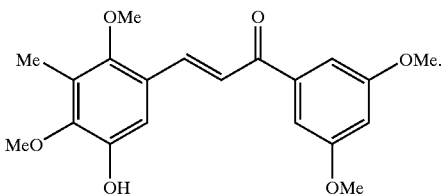

75. A method according to claim 43, wherein the proliferative condition is cancer.

76. A method of prophylactically treating a proliferative condition in a patient comprising administering to said patient a therapeutically-effective amount of a compound having the formula:

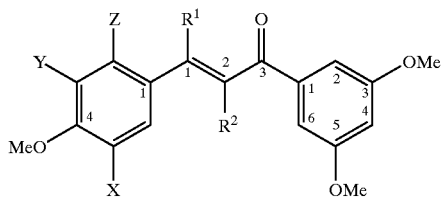

wherein:

X is —H, —OH, —OC(=O)R$^3$, —OS(=O)$_2$OH, or —OP(=O)(OH)$_2$;

Y is —H or a C$_{1-4}$alkyl group;

Z is —H or —OCH$_3$;

R$^1$ is —H, a C$_{1-4}$alkyl group, or C$_{1-4}$fluoroalkyl group;

R$^2$ is —H, a C$_{1-4}$alkyl group, or C$_{1-4}$fluoroalkyl group; and,

R$^3$ is —H, a C$_{1-6}$alkyl group, a C$_{3-20}$heterocyclyl group, or a C$_{5-20}$aryl group;

or a pharmaceutically acceptable salt, ester, or protected form thereof.

77. A method according to claim 76, wherein the proliferative condition is cancer.

78. A method of treating a inflammatory condition in a patient comprising administering to said patient a therapeutically-effective amount of a compound having the formula:

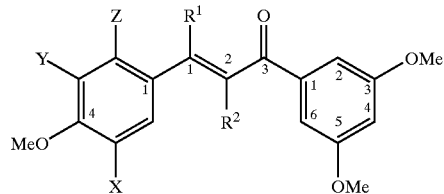

wherein:

X is —H, —OH, —OC(=O)R$^3$, —OS(=O)$_2$OH, or —OP(=O)(OH)$_2$;

Y is —H or a C$_{1-4}$alkyl group;

Z is —H or —OCH$_3$;

R$^1$ is —H, a C$_{1-4}$alkyl group, or C$_{1-4}$fluoroalkyl group;

R$^2$ is —H, a C$_{1-4}$alkyl group, or C$_{1-4}$fluoroalkyl group; and,

R$^3$ is —H, a C$_{1-6}$alkyl group, a C$_{3-20}$heterocyclyl group, or a C$_{5-20}$aryl group;

or a pharmaceutically acceptable salt, ester, or protected form thereof.

79. A method according to claim 78, wherein the inflammatory condition is rheumatoid arthritis, rheumatic fever, osteoarthritis, inflammatory bowel disease, psoriasis, or bronchial asthma.

80. A method of diagnosis of a patient for the presence of tumour cells expressing the CYP1B1 enzyme, comprising:

(a) administering to the patient a compound having the formula:

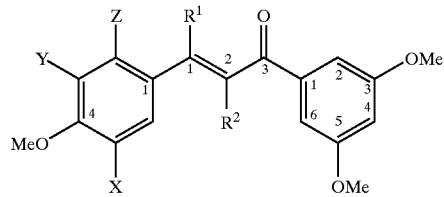

wherein:

X is —H;

Y is —H or a C$_{1-4}$alkyl group;

Z is —H or —OCH$_3$;

R$^1$ is —H, a C$_{1-4}$alkyl group, or C$_{1-4}$fluoroalkyl group;

R$^2$ is —H, a C$_{1-4}$alkyl group, or C$_{1-4}$fluoroalkyl group; and,

R$^3$ is —H, a C$_{1-6}$alkyl group, a C$_{3-20}$heterocyclyl group, or a C$_{5-20}$aryl group;

or a pharmaceutically acceptable salt, ester, or protected form thereof;

(b) determining the amount of the corresponding hydroxylated metabolite, wherein X is —OH, which is subsequently produced; and, (c) correlating the amount with the presence or absence of the tumour cells in the patient.

81. A compound of the formula:

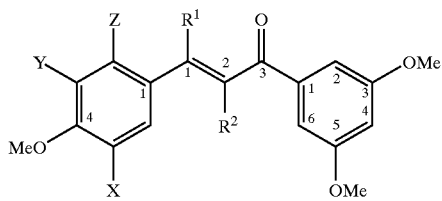

wherein:
X is —H, —OH, —OC(=O)R³, —OS(=O)₂OH, or —OP(=O)(OH)₂;
Y is —H or a C₁₋₄alkyl group;
Z is —H or —OCH₃;
R¹ is —H, a C₁₋₄alkyl group, or C₁₋₄fluoroalkyl group;
R² is —H, a C₁₋₄alkyl group, or C₁₋₄fluoroalkyl group; and,
R³ is —H, a C₁₋₆alkyl group, a C₃₋₂₀heterocyclyl group, or a C₅₋₂₀aryl group;
or a pharmaceutically acceptable salt, ester, or protected form thereof;
with the proviso that X, Y, Z, R¹, and R² are not all —H and at least two of X, Y and Z are not hydrogen when R¹ and R² are hydrogen.

82. A compound according to claim 1, wherein Z is —OCH₃ and X is —OH, —OC(=O)R³, —OS(=O)₂OH, or —OP(=O)(OH)₂.

83. A compound according to claim 1, wherein Z is —OCH₃ and Y is a C₁₋₄alkyl group.

84. A method of treating a proliferative condition in a patient comprising administering to said patient a therapeutically-effective amount of a compound of claim 81, or a pharmaceutically acceptable salt, ester, or protected form thereof.

85. A method of prophylactically treating a proliferative condition in a patient comprising administering to said patient a therapeutically-effective amount of a compound of claim 81 or a pharmaceutically acceptable salt, ester, or protected form thereof.

86. A method according to claim 85, wherein the proliferative condition is cancer.

87. A method of treating a inflammatory condition in a patient comprising administering to said patient a therapeutically-effective amount of a compound of claim 81 or a pharmaceutically acceptable salt, ester, or protected form thereof.

88. A method according to claim 87, wherein the inflammatory condition is rheumatoid arthritis, rheumatic fever, osteoarthritis, inflammatory bowel disease, psoriasis, or bronchial asthma.

89. A method of diagnosis of a patient for the presence of tumour cells expressing the CYP1B1 enzyme, comprising:
(a) administering to the patient a compound of claim 81, or a pharmaceutically acceptable salt, ester, or protected form thereof;
(b) determining the amount of the corresponding hydroxylated metabolite, wherein X is —OH, which is subsequently produced; and,
(c) correlating the amount with the presence or absence of the tumour cells in the patient.

* * * * *

UNITED STATES PATENT AND TRADEMARK OFFICE
CERTIFICATE OF CORRECTION

PATENT NO. : 6,787,672 B2  
APPLICATION NO. : 10/239757  
DATED : September 7, 2004  
INVENTOR(S) : Gerald Andrew Potter, Paul Crispin Butler, and Elugba Wanogho It is certified that error appears in the above-identified patent and that said Letters Patent is hereby corrected as shown below:

On Title Page, Item (86)

"PCT No. PCT/GB01/01341  
§ 371 (c)(1),  
(2), (4) Date: September 6, 2002" should read -- PCT No. PCT/GB01/01341  
§ 371 (c)(1),  
(2), (4) Date: September 26, 2002 --

Signed and Sealed this

Fourteenth Day of November, 2006

JON W. DUDAS  
*Director of the United States Patent and Trademark Office*